United States Patent
Swennen et al.

(10) Patent No.: US 11,357,520 B2
(45) Date of Patent: Jun. 14, 2022

(54) BONE POSITIONING DEVICE FOR DYSGNATHIA HAVING A CUTTING-TOOL GUIDE

(71) Applicant: KARL LEIBINGER MEDIZINTECHNIK GMBH & CO. KG, Mühlheim (DE)

(72) Inventors: Gwenn Swennen, Knokke (BE); Frank Reinauer, Emmingen-Liptingen (DE); Tobias Wolfram, Dreieich (DE); Adem Aksu, VS-Schwenningen (DE)

(73) Assignee: KARL LEIBINGER MEDIZINTECHNIK GMBH & CO. KG, Mühlheim (DE)

( * ) Notice: Subject to any disclaimer, the term of this patent is extended or adjusted under 35 U.S.C. 154(b) by 56 days.

(21) Appl. No.: 16/629,704

(22) PCT Filed: Jul. 12, 2018

(86) PCT No.: PCT/EP2018/068955
§ 371 (c)(1),
(2) Date: Jan. 9, 2020

(87) PCT Pub. No.: WO2019/012048
PCT Pub. Date: Jan. 17, 2019

(65) Prior Publication Data
US 2021/0085344 A1   Mar. 25, 2021

(30) Foreign Application Priority Data
Jul. 13, 2017   (DE) .................... 10 2017 115 750.6

(51) Int. Cl.
*A61B 17/17*   (2006.01)
*A61B 17/15*   (2006.01)
(Continued)

(52) U.S. Cl.
CPC .......... *A61B 17/176* (2013.01); *A61B 17/151* (2013.01); *A61B 2017/1602* (2013.01); *A61C 5/007* (2013.01)

(58) Field of Classification Search
CPC .................................................. A61B 17/176
See application file for complete search history.

(56) References Cited

U.S. PATENT DOCUMENTS 4,306,866 A     12/1981  Weissman
10,426,572 B2 * 10/2019  Tahmasebi ............. A61C 1/082
(Continued)

FOREIGN PATENT DOCUMENTS

CH   710 871      9/2016
CN   104771231    7/2015
(Continued)

OTHER PUBLICATIONS

Chinese Office Action dated Mar. 22, 2021 from Chinese Application No. 201880045747.5.
(Continued)

*Primary Examiner* — Nicholas W Woodall
(74) *Attorney, Agent, or Firm* — Beyer Law Group LLP

(57) ABSTRACT

The invention relates to a bone positioning device (1) for use in the repositioning of bone sections relative to each other in case of dysgnathia, comprising a main body (2), which has a bottom side (3), which faces the lower jaw (7) and in which there are recesses (5) for receiving navigating aids (6) fixed to the lower jaw, and an opposite top side (4), which faces the upper jaw and in which there are likewise recesses (5) for receiving navigating aids (6) fixed to the upper jaw, wherein at least one cutting-tool guide device (8) is attached to the main body (2).

9 Claims, 1 Drawing Sheet

(51) Int. Cl.
    *A61B 17/16*    (2006.01)
    *A61C 5/00*     (2017.01)

(56) References Cited

U.S. PATENT DOCUMENTS

| | | | |
|---|---|---|---|
| 11,007,035 B2* | 5/2021 | Fares | A61C 1/082 |
| 2004/0166469 A1 | 8/2004 | Tremont | |
| 2006/0240378 A1* | 10/2006 | Weinstein | A61B 5/1077 |
| | | | 433/76 |
| 2009/0274990 A1* | 11/2009 | Kim | A61B 17/176 |
| | | | 433/75 |
| 2011/0059413 A1 | 3/2011 | Schutyser et al. | |
| 2011/0311941 A1* | 12/2011 | Yi | A61C 1/084 |
| | | | 433/75 |
| 2012/0022604 A1* | 1/2012 | Polley | A61B 17/666 |
| | | | 606/86 R |
| 2013/0296872 A1* | 11/2013 | Davison | A61B 17/17 |
| | | | 606/87 |
| 2018/0235726 A1* | 8/2018 | Zastrow | A61C 8/0089 |
| 2020/0015934 A1* | 1/2020 | Llop | A61B 17/176 |

FOREIGN PATENT DOCUMENTS

| | | |
|---|---|---|
| CN | 105078586 | 11/2015 |
| CN | 204863356 | 12/2015 |
| CN | 105686886 | 6/2016 |
| DE | 10 2006 043 204 | 3/2008 |
| EP | 2 792 329 | 10/2014 |

OTHER PUBLICATIONS

German Search Report dated Feb. 14, 2018 from German Application No. 10 2017 115 750.6.
International Search Report dated Sep. 10, 2018 from International Application No. PCT/EP2018/068955.
Russian Office Action dated Oct. 20, 2021 from Russian Application No. 2020106679/14(010383).

* cited by examiner

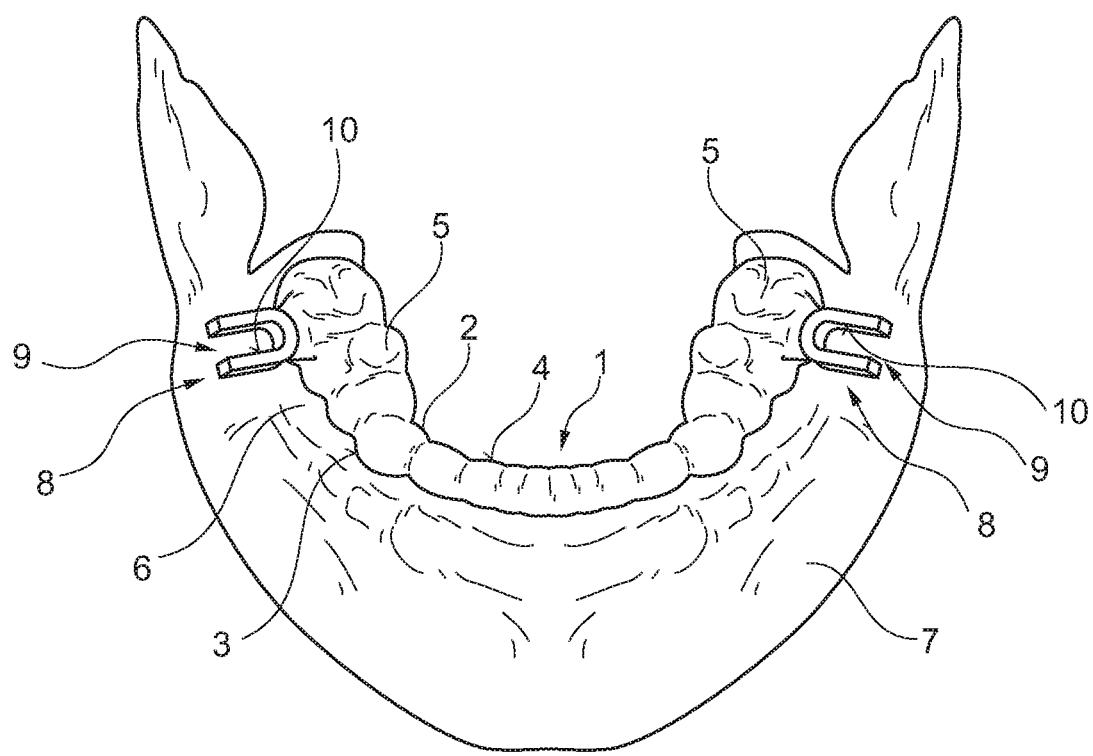

BONE POSITIONING DEVICE FOR DYSGNATHIA HAVING A CUTTING-TOOL GUIDE

The invention relates to a bone positioning device for use in dysgnathia when repositioning bone sections relative to each other. Such bone sections are then usually components of an upper jaw or a lower jaw. These bone sections are then completely separated from the remaining bone at a point where a cutting tool has made a separation. The bone positioning device has a base body having a bottom side facing the lower jaw, on which recesses are provided for accommodating navigation aids fixed to the lower jaw, such as teeth or gingival sections, and also has an opposite top side facing the upper jaw, on which recesses are also provided for accommodating navigation aids fixed to the upper jaw, such as teeth or gingival sections. Experts refer to such bone positioning devices as splints. Such splints or bone positioning devices are usually plastic splints, with which the upper and lower jaws are connected to each other intraoperatively, i.e. during surgery, in order to secure their position, the desired interlocking of teeth as well as the position of the condyles/jaw joint heads. In order to move the lower jaw into the desired position, a sagittal osteotomy is often performed. In this case, however, the separation is performed freely and without guidance. Unfortunately, this sometimes leads to an imprecise positional cut.

Bone positioning devices in general are known from the prior art. For example, US 2012/0022604 A1 discloses a skeletal positioning apparatus with a splint having a main body for coupling to a skeletal structure of a patient. Further, CN 104 771 231 A, CN 105 078 586 A and CN 105 686 886 A disclose a navigation device for bone block directional movement in an orthognathic surgery including a U-shaped bite plate.

It is the object of the present invention to perform surgery faster, with greater promise of success, and with greater precision. In particular, the disadvantages known from the state of the art should also be eliminated. A solution to be presented should be inexpensive, easy to implement and be able to assert itself well in the market.

According to a first aspect of the invention there is provided a bone positioning device for use in dysgnathia for repositioning bone sections relative to each other, having a base body which has a bottom side facing the lower jaw, wherein recesses for accommodating navigation aids fixed to the lower jaw are provided thereon, and an opposite top side facing the upper jaw, on which also recesses for accommodating navigation aids fixed to the upper jaw are provided, wherein at least one cutting-tool guide device is attached to the base body.

According to the invention, this object is solved in a generic bone positioning device, in that at least one cutting-tool guide device is attached to the base body, which is prepared to guide a cutting tool exactly along the desired position cut.

A lateral saw guide, which can be used in the field of dysgnathia, is thus provided on the splint for occlusion of the upper jaw to the lower jaw. A sagittal incision which is fit for trailing can then be made with a milling cutter or another desired cutting tool. This cut is then precise.

Advantageous embodiments are claimed in the dependent claims and are explained in more detail below.

It is advantageous if the cutting-tool guide device protrudes outwards and/or inwards. With a large number of cutting-tool guide devices, a certain number of them can protrude outwards and a certain number inwards. However, it is preferred if all cutting-tool guide devices protrude outwards or inwards. The cutting-tool guide device is intended to have a guide area that allows the insertion/application of a cutting tool, such as a milling cutter or a saw, in order to produce a slit which is 1 mm +/−20% thick. The direction can be transferred with a milling cutter, using the splint, and the osteotomy can be marked. The osteotomy is then also performed with a milling cutter. It can be the same milling cutter.

If the cutting-tool guide device defines a path along which a cutting tool, such as the milling cutter or the saw, is guided in a constrained manner, any straying or slipping of the cutting tool is effectively excluded.

In order to be able to cut through the bone as quickly as possible, it is advantageous if the path is completely or in sections linear/straight, whereby the alternative of a curved path is also conceivable, in particular to avoid critical areas. It is conceivable that the path is linear in sections and curved in sections. In the case of a curved design, a constant curvature, an increasing or decreasing curvature, or a combination of these designs can be used.

It has proven to be successful if the cutting-tool guide device has a horseshoe-shaped, U-, C- or L-shaped cross-section. This results in the insertion of a tool for being guided in several spatial directions, preferably three spatial directions. While an open structure is always used for horseshoe, U, C or L-shaped cross-sections, a closed structure, such as a hollow cylinder, can also be considered. In particular, a hollow cylinder with a polygon-like, elliptical or even circular inner or outer contour is conceivable.

It has also proved to be effective if a vector runs along the path transverse to an imaginary plane through the top side and/or the bottom side of the base body.

An advantageous embodiment is also characterized in that there are two cutting-tool guide devices on both sides of the base body. A complete separation of the lower jaw area to be relocated from the remaining lower jaw can then be quickly created. This applies to the upper jaw in the figurative sense.

It is beneficial for the manufacturing process if the cutting-tool guide device is connected to the base body integrally/in one piece/as a single material or if it is detachably connected to the base body, for example with a form fit and/or force fit. In the first case, a complete tool can be created that does not need further preparation, whereas in the second case, better handling is the result.

If a predetermined breaking point is provided/formed between the cutting-tool guide device and the base body, there are more operational possibilities of use.

It has also proven to be successful if the base body has a base, e.g. a square base, to which a counterpart accommodation is inserted/adapted on/in the cutting-tool guide device.

It is advantageous if an abrasion-prevention insert is provided in the area of a planned cutting tool contact. This increases the precision of the insert during surgery.

It is also advantageous if the abrasion-prevention device is made of harder material, at least on the surface/on a section of the surface, than the base body or the rest of the cutting-tool guide device.

An advantageous embodiment is also characterized in that the abrasion-prevention insert is clipped or glued in/on the cutting-tool guide device or in/on the base body.

Ultimately, the invention thus also relates to the application of the bone positioning device such that the cutting-tool guide device acts as a frame.

The invention can also be further developed by using resin/silicones and/or similar materials on the base body and/or the cutting-tool guide device. Generative/additive manufacturing processes can be used.

The surface of the cutting-tool guide device facing the cutting tool can be designed in the form of a step or a right angle or can include this/these. The orientation of the cutting-tool guide device, in particular of the vector assigned to the path already explained, is already determined during the virtual planning Thus, the orientation is already predetermined during the virtual planning As a background, it should be explained at this point that usually several bone positioning devices are used. Usually, a so-called actual state splint is used during surgery when the bone position is still incorrect. The present invention relates to this splint. The intermediate splint or the final splint inserted afterwards can be manufactured in the same way—but usually differently—since no milling or cutting processes are required anymore. Therefore, the cutting-tool guide device may be missing on this intermediate split or the final split.

Advantageous embodiments are claimed in the dependent claims and are explained in more detail below.

The only FIG. 1 shows a perspective view from the front of a bone positioning device/actual state splint according to the invention in the state placed on the teeth of the lower jaw. Furthermore, the bone positioning device with the cutting-tool guide device can be combined not only with the actual state splint but also with the respective temporary intermediate splint or the final splint. The different splint variants reflect the different positions of the jaw fragments during the individual steps of the repositioning osteotomy. With their help, the final occlusion is successively adjusted actively.

The FIGURE is merely schematic in nature and serves only to understand the invention.

In FIG. 1, a bone positioning device 1 according to the invention can be seen from the front and the top.

The bone positioning device 1 in FIG. 1 has a base body 2 with a bottom side 3 and a top side 4. Recesses 5 are provided to accommodate teeth. The recesses 5 are exactly adapted to the geometry of the teeth. The teeth then act as navigation aid 6. The respective teeth are, for example, ingrown/anchored in the lower jaw 7. Of course, dental implants can also serve as navigation aids 6.

Cutting-tool guide devices 8 protrude on both sides of the base body 2 towards the outside. The cutting-tool guide devices 8 have an inner side 9, on which a contact surface 10 is formed for a cutting tool, such as a milling cutter or a saw, which is not shown. This contact surface 10 can be harder than the base body 2 and/or the inside of the cutting-tool guide device 8. The cutting-tool guide device 8 extends straight along an unshown vector diagonally backwards towards the lower jaw 7. It provides the cut for the cutting tool that leads to cutting through the lower jaw 7.

LIST OF REFERENCE SIGNS 1 bone positioning device/actual state splint
2 base body
3 bottom side
4 top side
5 recess
6 navigation aid
7 lower jaw
8 cutting-tool guide device
9 inner side
10 contact surface

The invention claimed is:

1. Bone positioning device for use in dysgnathia for repositioning bone sections relative to each other, the bone positioning device having a base body a bottom side facing a lower jaw of a patient when the bone positioning device is installed, the bottom side having recesses for accommodating navigation aids fixed to the lower jaw, and an opposite top side facing a upper jaw of the patient when the bone positioning device is installed, the opposite top side also having recesses for accommodating navigation aids fixed to the upper jaw, wherein at least one cutting-tool guide device is attached to the base body, wherein the cutting-tool guide device directly protrudes outwards from the base body to guide a cutting tool to affect complete separation of the bone sections to be repositioned, and wherein the cutting-tool guide device prescribes a path along which a cutting tool is guided in a constrained manner, and wherein the cutting-tool guide has an open cross-section and is designed in such a way that a cutting tool is guided in three spatial directions.

2. Bone positioning device according to claim 1, wherein the path is linear/straight or curved.

3. Bone positioning device according to claim 2, wherein the cutting-tool guide device has a horseshoe-shaped, U-, or C-shaped cross-section.

4. Bone positioning device according to claim 1, wherein a vector runs along the path transverse to an imaginary plane through the bottom side and/or the top side of the base body.

5. Bone positioning device according to claim 1, wherein two cutting-tool guide devices are provided on opposing lateral sides of the base body.

6. Bone positioning device according to claim 1, wherein the cutting-tool guide device is integrally connected to the base body or is detachably connected to the base body.

7. Bone positioning device according to claim 1, wherein a predetermined breaking point is present between the cutting-tool guide device and the base body.

8. Bone positioning device according to claim 1, wherein the cutting-tool guide device comprises a contact surface comprising an abrasion prevention surface that is provided in the area of a planned cutting tool contact.

9. Bone positioning device according to claim 1, wherein the cross-section of the cutting-tool guide device is arranged in a plane parallel to an upper side of the base body and is open towards the outside.

* * * * *